United States Patent
Gouda et al.

(10) Patent No.: US 10,801,959 B2
(45) Date of Patent: Oct. 13, 2020

(54) OBJECTIVE BIOLOGICAL SUBSTANCE ANALYSIS DEVICE, ANALYSIS SYSTEM, ANALYSIS METHOD, AND RECORDING MEDIUM STORING COMPUTER READABLE ANALYSIS PROGRAM

(71) Applicant: KONICA MINOLTA, INC., Chiyoda-ku (JP)

(72) Inventors: Hideki Gouda, Nerima-ku (JP); Yasuhiro Watanabe, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 137 days.

(21) Appl. No.: 15/737,124

(22) PCT Filed: Jun. 7, 2016

(86) PCT No.: PCT/JP2016/066926
§ 371 (c)(1),
(2) Date: Dec. 15, 2017

(87) PCT Pub. No.: WO2016/204027
PCT Pub. Date: Dec. 22, 2016

(65) Prior Publication Data
US 2018/0172589 A1    Jun. 21, 2018

(30) Foreign Application Priority Data

Jun. 18, 2015 (JP) ................................ 2015-122568
Jan. 20, 2016 (JP) ................................ 2016-008592

(51) Int. Cl.
*G01N 21/64* (2006.01)
*G01N 33/48* (2006.01)
(Continued)

(52) U.S. Cl.
CPC ............ *G01N 21/6428* (2013.01); *G01N 1/30* (2013.01); *G01N 21/64* (2013.01); *G01N 33/48* (2013.01);
(Continued)

(58) Field of Classification Search
CPC ...... G01N 21/6428; G01N 1/30; G01N 21/64; G01N 33/48; G01N 33/582; G01N 33/587; G01N 2021/6439
See application file for complete search history.

(56) References Cited

U.S. PATENT DOCUMENTS

2002/0018649 A1* 2/2002 Hakamata ............ H04N 5/3725
                                                            396/17
2003/0218137 A1* 11/2003 Sendai ................. A61B 5/0071
                                                            250/461.1
(Continued)

FOREIGN PATENT DOCUMENTS

JP        2009-9290       1/2009
JP       2010-281637     12/2010
(Continued)

OTHER PUBLICATIONS

Google Scholar Search Results.*
(Continued)

*Primary Examiner* — Qun Shen
(74) *Attorney, Agent, or Firm* — Cozen O'Connor

(57) ABSTRACT

An analysis device for an objective biological substance includes a generator, a divider, an analyzer, and a calculator. The generator generates a microscopic image of a tissue sample after staining. The divider divides the microscopic image into at least one section having a prescribed size. The analyzer analyzes a staining condition of the microscopic image for each section. The calculator calculates a prescribed statistic based on an analysis result by the analyzer.

13 Claims, 12 Drawing Sheets

(51) Int. Cl.
*G01N 33/58* (2006.01)
*G01N 1/30* (2006.01)

(52) U.S. Cl.
CPC ......... *G01N 33/582* (2013.01); *G01N 33/587* (2013.01); *G01N 2021/6439* (2013.01)

(56) References Cited

U.S. PATENT DOCUMENTS

| | | | | |
|---|---|---|---|---|
| 2003/0223626 | A1* | 12/2003 | Hansen | G06T 7/44 |
| | | | | 382/128 |
| 2005/0058352 | A1* | 3/2005 | Deliwala | G01J 3/0229 |
| | | | | 382/232 |
| 2007/0159627 | A1* | 7/2007 | Johnson | G01N 15/1463 |
| | | | | 356/335 |
| 2011/0212486 | A1* | 9/2011 | Yamada | G02B 21/365 |
| | | | | 435/40.5 |
| 2011/0282143 | A1* | 11/2011 | Matsumoto | G02B 23/2461 |
| | | | | 600/109 |
| 2012/0082366 | A1 | 4/2012 | Marugame | |
| 2013/0128024 | A1* | 5/2013 | Kishima | H04N 7/002 |
| | | | | 348/79 |
| 2013/0136324 | A1 | 5/2013 | Sakamoto et al. | |
| 2013/0136325 | A1* | 5/2013 | Sakamoto | G06T 7/0012 |
| | | | | 382/128 |
| 2013/0157895 | A1* | 6/2013 | Aimiya | G01N 1/30 |
| | | | | 506/9 |
| 2013/0235258 | A1* | 9/2013 | Shida | A61B 1/00186 |
| | | | | 348/370 |
| 2014/0184769 | A1* | 7/2014 | Ishihara | A61B 1/00009 |
| | | | | 348/68 |
| 2015/0086103 | A1* | 3/2015 | Tsunomori | G06T 7/0012 |
| | | | | 382/133 |
| 2015/0302237 | A1* | 10/2015 | Ohya | G01N 15/1475 |
| | | | | 382/133 |
| 2016/0003814 | A1* | 1/2016 | Hamasaki | G01N 21/6486 |
| | | | | 435/287.2 |

FOREIGN PATENT DOCUMENTS

| | | |
|---|---|---|
| JP | 2013-108926 | 6/2013 |
| JP | 2013-113680 | 6/2013 |
| JP | 5768945 | 8/2015 |
| JP | 5835536 | 12/2015 |
| JP | 2016-1141 | 1/2016 |
| WO | WO 2013/146694 | 10/2013 |
| WO | WO 2013/146843 | 10/2013 |
| WO | WO2015/146938 | 10/2015 |

OTHER PUBLICATIONS

Preliminary Report on Patentability and Written Opinion dated Dec. 19, 2017 which issued in the corresponding International Patent Application No. PCT/JP2016/066926.
Search Report dated Feb. 15, 2018 which issued in the corresponding European Patent Application No. 16811502.0.
Office Action dated Jan. 27, 2020 issued in Japanese Patent Application No. 2017-525160.

* cited by examiner

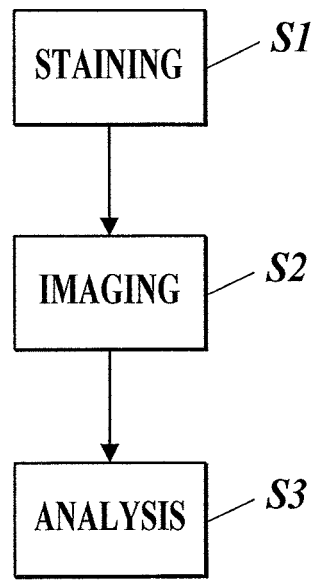
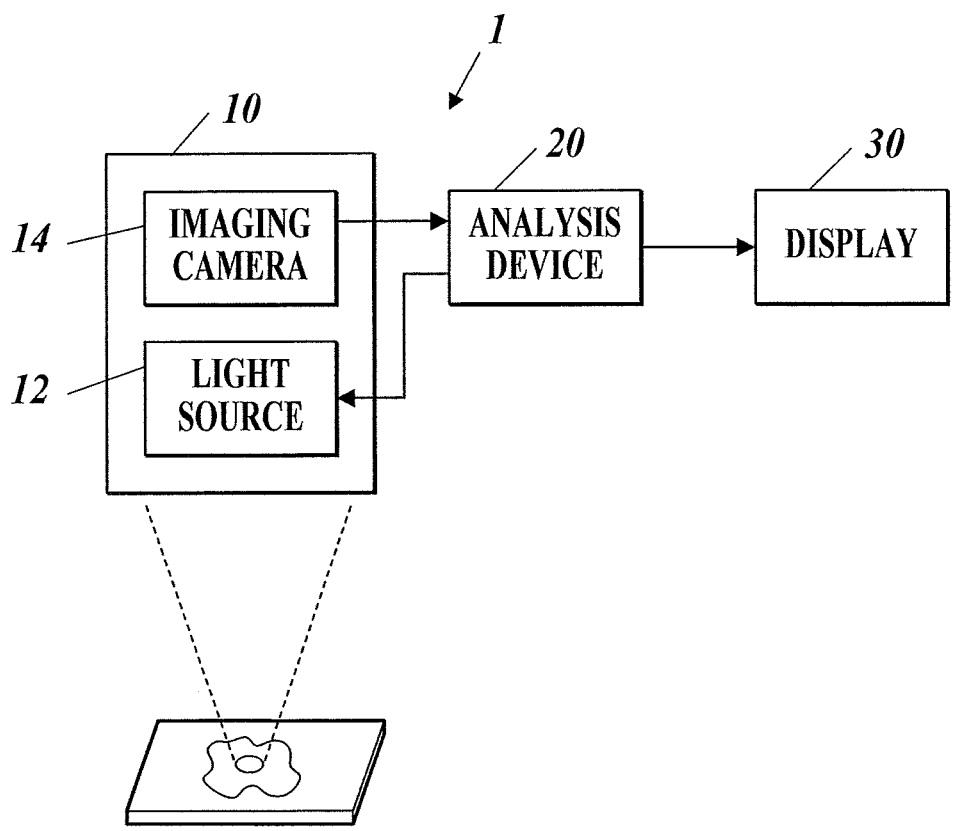

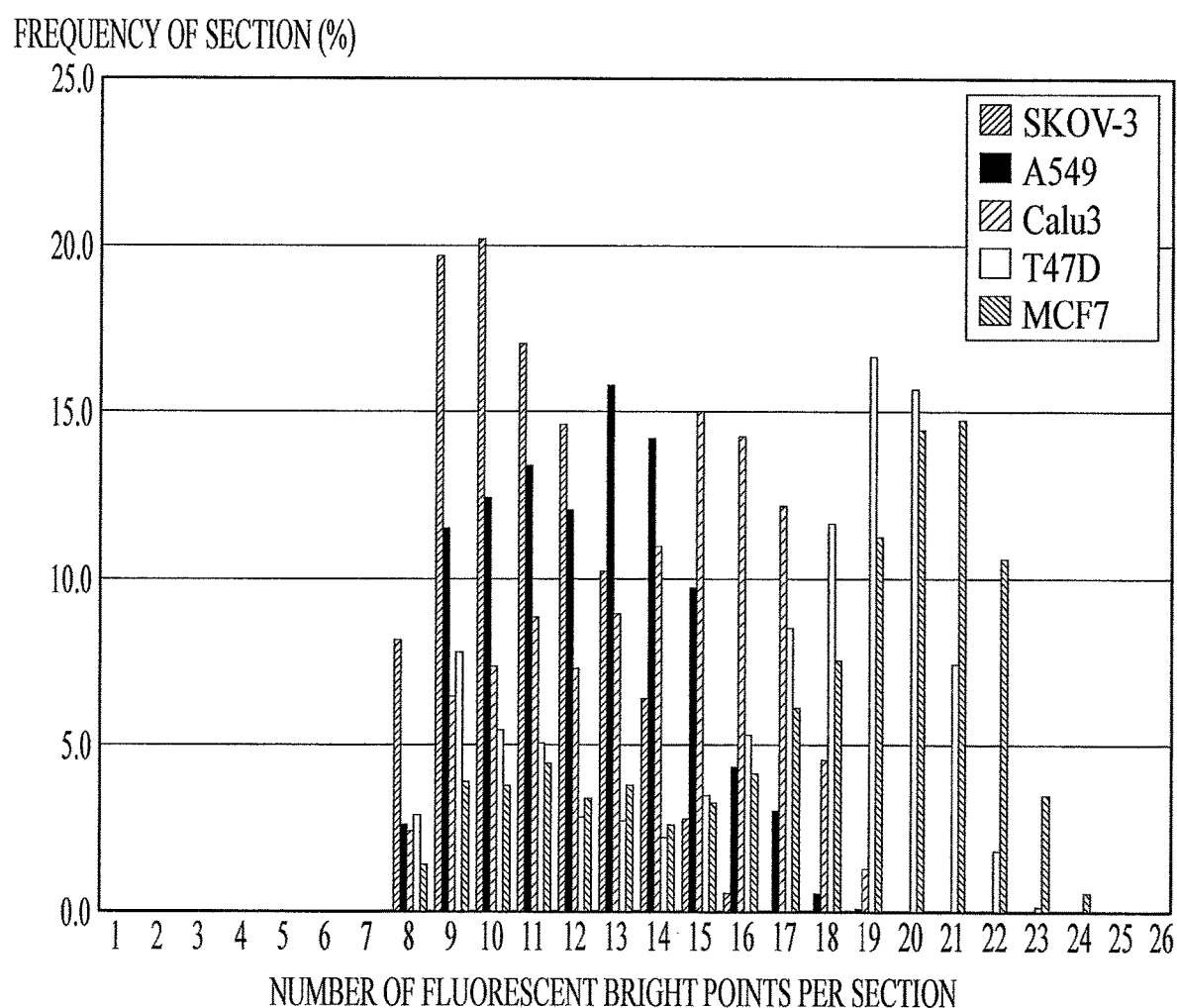

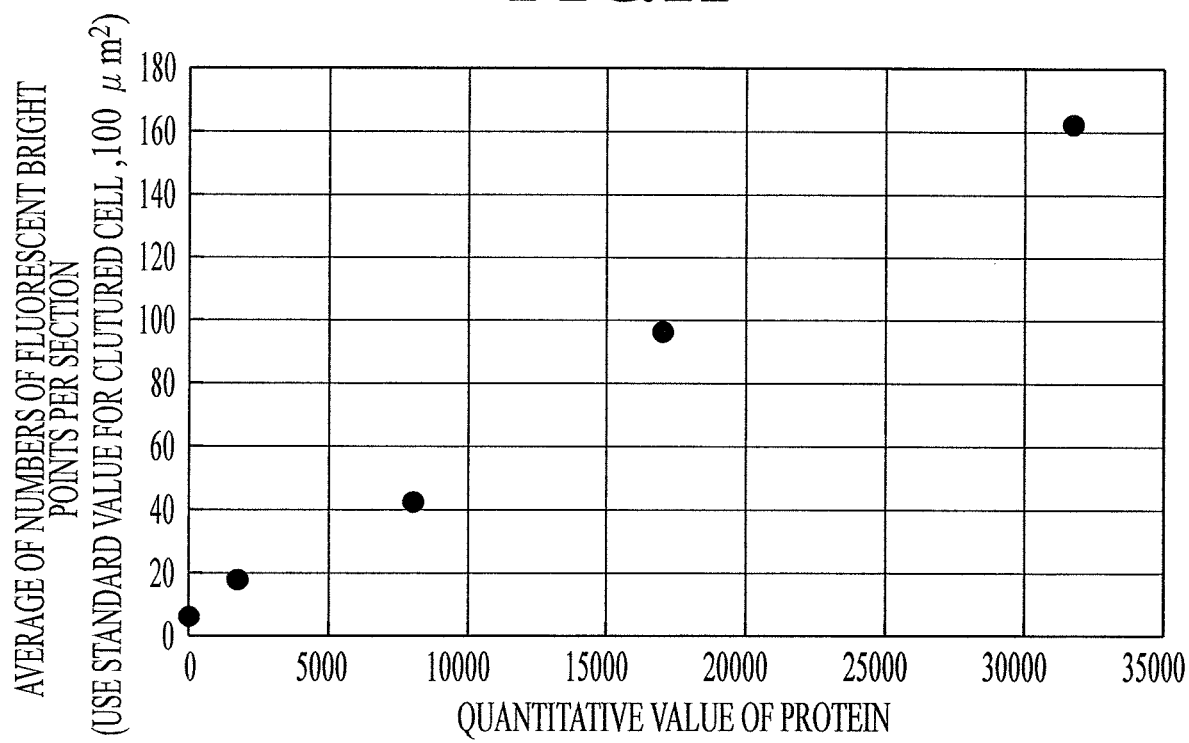

OBJECTIVE BIOLOGICAL SUBSTANCE ANALYSIS DEVICE, ANALYSIS SYSTEM, ANALYSIS METHOD, AND RECORDING MEDIUM STORING COMPUTER READABLE ANALYSIS PROGRAM

RELATED APPLICATIONS

This is a U.S. National Phase Application under 35 USC 371 of International Application PCT/JP2016/066926 filed on Jun. 7, 2016.

This application claims the priority of Japanese application nos. 2015-122568 filed Jun. 18, 2015 and 2016-008592 filed Jan. 20, 2016, the entire content of both of which are hereby incorporated by reference.

TECHNOLOGICAL FIELD

The present invention relates to an analysis device, an analysis system, an analysis method, and an analysis program for an objective biological substance.

BACKGROUND ART

An appropriate diagnosis is required for an appropriate treatment. A pathological diagnosis plays an important role as a final diagnosis. In the "pathological diagnosis", the kind or properties of a lesion is discriminated mainly by a microscopic examination of a part of tissue collected from a diseased part of a patient, in order to determine the course of treatment and to evaluate the effects of the treatment.

The applicant of the present invention discloses useful techniques for pathological diagnosis in Patent Document 1.

The techniques according to Patent Document 1 include the followings: acquiring a bright field image showing a shape of a cell in a tissue slice and a fluorescent image showing expression of a specific protein in a same range of the tissue slice as a fluorescent bright point; estimating a cell region including a region expressing a specific protein in the bright field image; and extracting fluorescent bright points from the fluorescent image. A feature amount is calculated for each cell region on the basis of the cell nucleus in the estimated cell region and the fluorescent bright points. On the basis of the feature amount, it is determined whether each cell region is cancerous or not and what the expression state of the specific protein is.

In recent years, even when a plurality of cells overlap with each other in the tissue sample (in the bright field image), it can be determined to which cell the fluorescent bright point in the fluorescent image belongs. As a result, the number of the expressing specific protein molecules can be precisely quantitated and the accuracy in pathological diagnosis is thereby improved (see paragraphs [0069] to [0080] and [0096] and FIG. 9 to FIG. 15 of Patent Document 2).

PRIOR ART DOCUMENT

Patent Document

Patent Document 1: International Publication No. 2013/146843

Patent Document 2: Japanese Patent Application No. 2014-121078

SUMMARY

Problems to be Solved by the Invention

However, the form (shape, size, and the like) of cells is different depending on the kind of cell line in tissue slice. Furthermore, a diagnostician is required to perform operations in extracting cell regions from the bright field image and in determining the cell to which the fluorescent bright point in the fluorescent image belongs. Even though software specialized for pathological diagnosis is used in the techniques disclosed in Patent Documents 1 and 2, there may be variations in diagnosis results depending on the kind of cell line in tissue slice and the diagnostician, and it takes time to analyze the cell to which the fluorescent bright point in the fluorescent image belongs.

FIG. 15 shows an exemplary result of a correlation between the quantitative value of protein and the number of fluorescent bright points per cell, calculated from sample tissue slices including five kinds of cell lines (SKOV-3, A549, Calu3, T47D, and MCF7) by a plurality of diagnosticians using the method of Patent Documents 1 and 2 and the like. "SKOV-3" is a cell line derived from human ovarian cancer cells, "A549" is a cell line derived from human lung cancer cells, "Calu3" is a cell line derived from human lung cells, "T47D" is a cell line derived from human breast adenocarcinoma cancer cells, and "MCF7" is a cell line derived from human breast cancer cells. The "quantitative value of protein" on horizontal axis in FIG. 15 is a luminance (a.u.) per cell measured by flow cytometric method. In measuring the "number of fluorescent bright points per cell" on vertical axis in FIG. 15, the processes from preparing tissue samples to obtaining fluorescent images of fluorescent bright points were performed according to the disclosure of Patent Documents 1 and 2. The processes are also described in the first embodiment ([STAINING STEP] and [IMAGING STEP]) of the present specification described below. Fluorescent images were obtained by immunostaining using an immunostaining reagent prepared by binding of anti-HER2 antibody, which specifically binds to HER2 protein on the surface of cells, to nanoparticles in which fluorescent substances are accumulated. Number of fluorescent bright points per cell was measured using software specialized for pathological diagnosis.

The black points in FIG. 15 represent the average of the numbers of fluorescent bright points and the bars extending from the black points upward and downward represent standard deviation. As shown in FIG. 15, the larger the quantitative value of protein is, the larger the standard deviation of the fluorescent bright points is. This reveals variations in diagnosis results (statistics) depending on the kind of cell line in tissue slice and the diagnostician.

Accordingly, the main object of the present invention is to provide an analysis device, an analysis system, an analysis method, and an analysis program for an objective biological substance which can shorten the analysis time while suppressing variations in statistic depending on the kind of tissue slice and the diagnostician.

Further object of the present invention includes measurement of nucleic acids, sugar chains, and enzymes, which are objective biological substances as well as proteins, through observation of fluorescent bright points in tissue slices.

Means for Solving the Problem

In order to solve the above-mentioned problems, according to the first embodiment of the present invention, there is provided an analysis device for an objective biological substance, including a generator that generates a microscopic image of a tissue sample after staining; a divider that divides the microscopic image into at least one section having a prescribed size; an analyzer that analyzes a staining condition of the microscopic image for each section; and a calculator that calculates a prescribed statistic based on an analysis result by the analyzer.

In order to solve the above-mentioned problems, according to the second embodiment of the present invention, there is provided an analysis system for an objective biological substance, including: a microscope that images a tissue sample after staining; and the analysis device for the objective biological substance according to any one of claims 1 to 11 that receives an imaging result by the microscope.

In order to solve the above-mentioned problems, according to the third embodiment of the present invention, there is provided an analysis method for an objective biological substance, including: generating a microscopic image of a tissue sample after staining; dividing the microscopic image into at least one section having a prescribed size; analyzing staining condition of the microscopic image for each section; and calculating a prescribed statistic based on an analysis result in the analyzing.

In order to solve the above-mentioned problems, according to the fourth embodiment of the present invention, there is provided an analysis program for an objective biological substance causing a computer to function as: a generator that generates a microscopic image of a tissue sample after staining; a divider that divides the microscopic image into at least one section having a prescribed size; an analyzer that analyzes a staining condition of the microscopic image for each section; and a calculator that calculates a prescribed statistic based on an analysis result by the analyzer.

According to the present invention, the analysis time can be shortened while suppressing variations in statistic depending on the kind of tissue slice and the diagnostician.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, and wherein:

FIG. 1 is a schematic diagram of steps in an analysis method for an objective biological substance;

FIG. 2 is a diagram of a schematic configuration of an analysis system for an objective biological substance;

FIG. 9 is a diagram illustrating an exemplary histogram of sections including a certain number of fluorescent bright points relative to all sections;

FIG. 11 is a diagram illustrating an exemplary correlation diagram of a statistic (average) according to the second embodiment and a quantitative value of protein;

EMBODIMENT FOR CARRYING OUT THE INVENTION

Figure 3A:
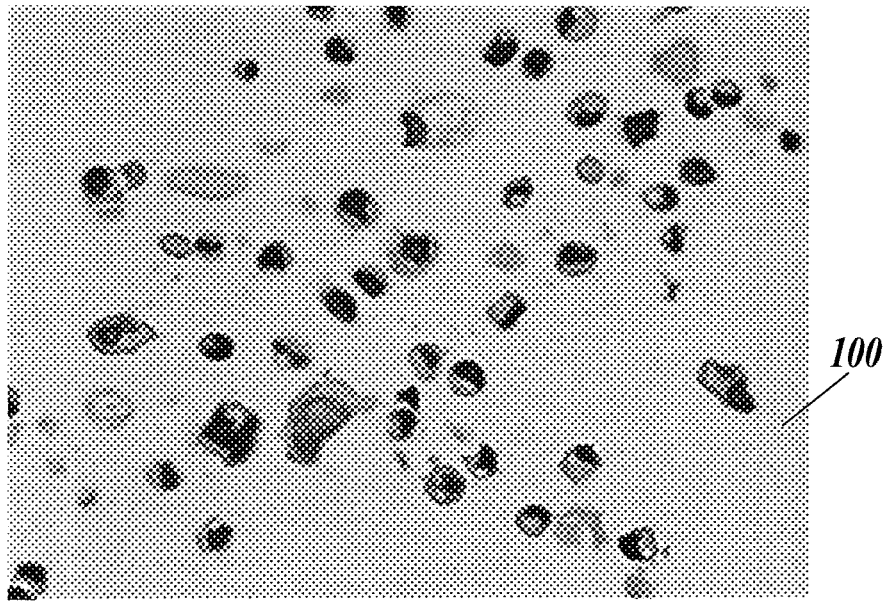
FIG. 3A is a diagram illustrating an exemplary bright field image.

Hereinafter, preferred embodiments of the present invention are described with reference to the drawings.

First Embodiment

In the present embodiment, an analysis method is provided for calculating a prescribed statistic through analysis of microscopic images. The method includes the following steps as shown in FIG. 1;
(S1) a step of staining a tissue sample with a predetermined staining reagent;
(S2) a step of imaging a stained image of the tissue sample after staining with a prescribed microscopy; and
(S3) a step of calculating the prescribed statistic through analysis of the microscopic image.

The staining step S1 is explained first, and subsequently the imaging step S2 and the analysis step S3 are explained. Analysis system 1 illustrated in FIG. 2 is used in the imaging step S2 and analysis step S3, in particular.

[Staining Step]

In the staining step S1, a tissue sample A including an objective biological substance is prepared. Immunostaning and morphological observation staining of the tissue sample A are performed using a staining reagent for immunostaining and a staining reagent for morphological observation.

(1) Objective Biological Substance

Objective biological substance is a target to be immunostained with a fluorescent marker for detection and quantitation mainly from the viewpoint of pathological diagnosis and includes a biological substance expressed in a tissue slice (in particular, protein (antigen), nucleic acid (for example, DNA, RNA, and miRNA), and the like).

A typical example of the objective biological substance includes a biological substance expressed on cell membrane in a variety of cancer tissues and used as a biomarker.

[Binding of Biological Substance Recognition Site to Fluorescent Nanoparticle]

The biological substance recognition site according to the present embodiment is a site specifically bindable or reactive to a target biological substance. The target biological substance may be any biological substance specifically bindable to the site. Typical examples of the target biological substance include proteins (peptides), nucleic acids (oligonucleotides, polynucleotides), and antibodies. Accordingly, examples of a substance specifically bindable to the target biological substance include antibodies that can recognize the proteins as antigens, other proteins specifically bindable to the proteins, and nucleus acids having base sequences allowing hybridization to the nucleus acids. Specific examples thereof include an anti-HER2 antibody specifically bindable to HER2, which is a protein on surfaces of cells; an anti-ER antibody specifically bindable to an estrogen receptor (ER), which is present in cell nuclei; and an anti-actin antibody specifically bindable to actin that forms a cell skeleton. Among these antibodies, the anti-HER2 antibody and the anti-ER antibody are preferred because a fluorescent particle bonded to them can be used in selection of drugs for breast cancer.

Examples of the specific antigens include the followings. The antibodies for recognizing these antigens are commercially available from a variety of antibody manufacturers, and can also be produced based on knowledge generally shared. Examples of the specific antigens include M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, c-MET, collagen type IV, Cox-2, cyclin D1, keratin, cytokeratin (high molecular weight), pan-keratin, pan-keratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, factor VIII-related antigen, fascin, FSH, galectin-3, gastrin, GFAP, glucagon, glycophorin A, granzyme B, hCG, hGH, *Helicobacter pylori*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, P63, PAX 5, PLAP, *Pneumocystis carinii*, Podoplanin (D2-40), PGR, prolactin, PSA, prostatic acid phosphatase, renal cell carcinoma, S100, somatostatin, spectrin, synaptophysin, TAG-72, TdT, thyroglobulin, TSH, TTF-1, TRAcP, tryptase, bilin, vimentin, WT1, and Zap-70.

In the case where the target biological substance is a nucleus acid, the following specific nucleus acid genes whose relations with diseases are pointed out can be exemplified. Probes recognizing these specific nucleus acid genes are commercially available as BAC probes, and can also be produced based on knowledge generally shared. Specific examples of the specific nucleus acid genes are listed below. Examples of genes related to proliferation of cancer or response rates of molecular target drugs include HER2, TOP2A, HER3, EGFR, P53, and MET. Known examples of cancer related genes are as follows. Examples of tyrosine kinase related genes include ALK, FLT3, AXL, FLT4 (VEGFR3, DDR1, FMS(CSF1R), DDR2, EGFR(ERBB1), HER4(ERBB4), EML4-ALK, IGF1 R, EPHA1, INSR, EPHA2, IRR(INSRR), EPHA3, KIT, EPHA4, LTK, EPHA5, MER(MERTK), EPHA6, MET, EPHA7, MUSK, EPHA8, NPM1-ALK, EPHB1, PDGFRα(PDGFRA), EPHB2, PDGFRβ(PDGFRB)EPHB3, RET, EPHB4, RON (MST1R), FGFR1, ROS(ROS1), FGFR2, TIE2(TEK), FGFR3, TRKA(NTRK1), FGFR4, TRKB(NTRK2), FLT1 (VEGFR1), and TRKC(NTRK3). Examples of breast cancer related genes include ATM, BRCA1, BRCA2, BRCA3, CCND1, E-Cadherin, ERBB2, ETV6, FGFR1, HRAS, KRAS, NRAS, NTRK3, p53, and PTEN. Examples of genes related to carcinoid tumors include BCL2, BRD4, CCND1, CDKN1A, CDKN2A, CTNNB1, HES1, MAP2, MEN1, NF1, NOTCH1, NUT, RAF, SDHD, and VEGFA. Examples of colorectal cancer related genes include APC, MSH6, AXIN2, MYH, BMPR1A, p53, DCC, PMS2, KRAS2 (or Ki-ras), PTEN, MLH1, SMAD4, MSH2, STK11, and MSH6. Examples of lung cancer related genes include ALK, PTEN, CCND1, RASSF1A, CDKN2A, RB1, EGFR, RET, EML4, ROS1, KRAS2, TP53, and MYC. Examples of liver cancer related genes include Axin1, MALAT1, b-catenin, p16 INK4A, c-ERBB-2, p53, CTNNB1, RB1, Cyclin D1, SMAD2, EGFR, SMAD4, IGFR2, TCF1, and KRAS. Examples of kidney cancer related genes include Alpha, PRCC, ASPSCR1, PSF, CLTC, TFE3, p54nrb/NONO, and TFEB. Examples of thyroid cancer related genes include AKAP10, NTRK1, AKAP9, RET, BRAF, TFG, ELE1, TPM3, H4/D10S170, and TPR. Examples of ovarian cancer related genes include AKT2, MDM2, BCL2, MYC, BRCA1, NCOA4, CDKN2A, p53, ERBB2, PIK3CA, GATA4, RB, HRAS, RET, KRAS, and RNASET2. Examples of prostate cancer related genes include AR, KLK3, BRCA2, MYC, CDKN1B, NKX3.1, EZH2, p53, GSTP1, and PTEN. Examples of bone tumor related genes include CDH11, COL12A1, CNBP, OMD, COL1A1, THRAP3, COL4A5, and USP6.

The biological substance recognition site may be bonded to a fluorescent nanoparticle with any bond. Examples of the bonding form include covalent bond, ionic bond, hydrogen bond, coordination bond, physical adsorption, and chemical adsorption. Bonds having strong forces, such as covalent bond, are preferred in view of stability of the bond.

(2) Immunostaining Reagent (Conjugate of Antibody and Fluorescent Nanoparticle)

As an immunostaining reagent, it is preferable to use a complex including a fluorescent nanoparticle bonded to a primary antibody with a bond other than a covalent bond, that is, an indirect bond such as antibody-antigen interaction. The efficiency of fluorescent labelling can be thereby improved and the time resulting in deterioration of fluorescence can be suppressed. For easy staining operation, as an immunostaining reagent, it is possible to use a complex including a fluorescent nanoparticle directly bonded to a primary antibody or secondary antibody.

An exemplary immunostaining reagent may be described as follows: [a primary antibody against the objective biological substance] . . . [an antibody (secondary antibody) against the primary antibody]~[a fluorescent nanoparticle]

" . . . " represents a bond with an antibody-antigen interaction. "~" represents a non-limited bond, for example, a covalent bond, an ionic bond, a hydrogen bond, a coordination bond, an antibody-antigen interaction, an avidin-biotin interaction, physical adsorption, and chemical adsorption, if necessary, via a linker molecule, (3) Antibody An antibody (IgG) which can be used as a primary antibody specifically recognizes and binds to an objective biological substance (protein) as an antigen. For example, anti-HER2 antibody can be used when HER2 is the objective biological substance, and anti-HER3 antibody can be used when HER3 is the objective biological substance.

An antibody (IgG) which can be used as a secondary antibody specifically recognizes and binds to an primary antibody.

Both primary antibody and secondary antibody may be polyclonal antibodies, but preferably monoclonal antibodies from the viewpoint of stable quantitation. Animals used for producing antibody (immunized animal) is not particularly limited, and can be selected from any conventionally used animals, such as mouse, rat, rabbit, coat, and sheep.

(4) Fluorescent Nanoparticle

The fluorescent nanoparticle is a nano-sized particle which emits fluorescence in response to irradiation of excitation light. The fluorescent nanoparticle can emit sufficiently strong fluorescence so that each molecule of the objective biological substance is represented as a fluorescent bright point.

Preferably used fluorescent nanoparticle includes a quantum dot (a semiconductor nanoparticle) and a nanoparticle having accumulated fluorescent substances.

(4.1) Quantum Dot

The quantum dot may be a semiconductor nanoparticle containing Group II-VI compounds, Group III-V compounds, or Group IV elements. Specific examples thereof include CdSe, CdS, CdTe, ZnSe, ZnS, ZnTe, InP, InN, InAs, InGaP, GaP, GaAs, Si, and Ge.

(4.2) Nanoparticle Having Accumulated Fluorescent Substances

The nanoparticle having accumulated fluorescent substances is a nano-sized particle containing an organic or inorganic particle as a base material and further having a plurality of fluorescent substances (for example, above-described quantum dots and fluorescent dyes) in the particle and/or on the surface of the particle.

The nanoparticle having accumulated fluorescent substances preferably contains a base material and fluorescent substances which has a substituent group or a site having opposite electric charge from each other to cause an electrostatic interaction.

The nanoparticle having accumulated fluorescent substances includes a nanoparticle having accumulated quantum dots and a nanoparticle having accumulated fluorescent dye.

(4.2.1) Base Material

Examples of an organic base material include resins commonly classified into thermosetting resins, such as melamine resins, urea resins, aniline resins, guanamine resins, phenol resins, xylene resins, and furan resins; resins commonly classified into thermoplastic resins, such as styrene resins, acrylic resins, acrylonitrile resins, AS resins (acrylonitrile-styrene copolymer resin), and ASA resins (acrylonitrile-styrene-acrylic resins); other resins such as polylactic acid resins; and polysaccharides.

Examples of an inorganic base material include silica, glass, and the like.

(4.2.2) Nanoparticle Having Accumulated Quantum Dots

The nanoparticle having accumulated quantum dots contains the above-described quantum dots in the base material and/or on the surface of the base material.

If the quantum dots are in the base material, the quantum dots may be dispersed within the base material in any form. The quantum dots and the base material may or may not be chemically bonded with each other.

(4.2.3) Nanoparticle Having Accumulated Fluorescent Dye

The nanoparticle having accumulated fluorescent dye contains fluorescent dye in the base material and/or on the surface of the base material.

Examples of the fluorescent dye include rhodamine-based dye molecules, squarylium-based dye molecules, cyanine-based dye molecules, aromatic ring-based dye molecules, oxazine-based dye molecules, carbopyronine-based dye molecules, and pyrromethene-based dye molecules.

Examples of the fluorescent dye include Alexa Fluor (registered trademark, made by Invitrogen Corporation) dye molecules, BODIPY (registered trademark, made by Invitrogen Corporation) dye molecules, Cy (registered trademark, made by GE Healthcare) dye molecules, HiLyte (registered trademark, made by AnaSpec Inc.) dye molecules, DyLight (registered trademark, made by Thermo Scientific Inc.) dye molecules, ATTO (registered trademark, made by ATTO-TEC GmbH.) dye molecules, MFP (registered trademark, made by Mobitec Inc.) dye molecules, CF (registered trademark, made by Biotium Inc.) dye molecules, DY (registered trademark, made by Dyomics GmbH) dye molecules, CAL (registered trademark, made by Bio-Search TechnologiesInc.) dye molecules, and the like.

Exemplary specific names of the specific fluorescent dyes are as follows: 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine; Sulforhodamine B, Sulforhodamine 101, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, and BODIPY 650/665 (these are manufactured by Invitrogen Corporation); methoxycoumarin, eosin, NBD, pyrene, Cy5, Cy5.5, Cy7, HiLyte Fluor 594 (registered trademark, made by AnaSpec Inc.), DyLight 594 (registered trademark, made by Thermo Scientific Inc.) dye molecules, ATTO 594 (registered trademark, made by ATTO-TEC GmbH.), MFP 594 (registered trademark, made by Mobitec Inc.), 5,10,15,20-Tetraphenylporphine tetrasulfonic acid, zinc 5,10,15,20-Tetraphenylporphine tetrasulfonic acid, phthalocyanine tetrasulfonic acid, zinc phthalocyanine tetrasulfonic acid, N,N-Bis-(2,6-diisopropylphenyl)-1,6,7,12-(4-tert-butylphenoxy)-perylen-3,4,9,10-tetracarbonaciddiimide, N,N'-Bis(2,6-diisopropylphenyl)-1,6,7,12-tetraphenoxyperylene-3,4,9,10-tetracarboxdiimide, Benzenesulfonic acid, 4,4',4'',4'''-[(1,3,8,10-tetrahydro-1,3,8,10-tetraoxoperylo[3,4-cd:9,10-c'd'] dipyran-5,6,12,13-tetrayl)tetralis(oxy)]tetrakis, and the like. These dyes may be used alone or in combination of two or more.

If the fluorescent dye is included in the base material, the fluorescent dye may be dispersed within the base material in any form. The fluorescent dye and the base material may or may not be chemically bonded with each other.

(5) Staining Method of Tissue Slice

An exemplary staining method will now be described.

A tissue slice (hereinafter may be simply referred to as a "slice" and includes a slice such as a pathological slice)

prepared by any known procedures can be applied to the staining method described below.

(5.1) Preparation of Tissue Sample (5.1.1) Deparaffinization Process

A slice is immersed in a container containing xylene so that paraffin is removed. The temperature is not particularly limited, and the processing can be performed at room temperature. Preferably, the immersing time is 3 minutes or more and 30 minutes or less. The xylene may be changed during the immersion as needed.

Next, the slice is immersed in a container containing ethanol so that the xylene is removed. The temperature is not particularly limited, and the processing can be performed at room temperature. Preferably, the immersing time is 3 minutes or more and 30 minutes or less. The ethanol may be changed during the immersion as needed.

The slice is immersed in a container containing water so that the ethanol is removed. The temperature is not particularly limited, and the processing can be performed at room temperature. Preferably, the immersing time is 3 minutes or more and 30 minutes or less. The water may be changed during the immersion as needed.

(5.1.2) Retrieval Process

In accordance with a known method, the objective biological substance is subjected to retrieval process. The retrieval process can be performed under any condition without limitation. As for a retrieving solution, a 0.01 M citrate buffer solution (pH 6.0), a 1 mM EDTA solution (pH 8.0), 5% urea, a 0.1 M Tris-hydrochloride buffer solution, or the like can be used.

The retrieval process is performed under a condition of pH 2.0 to 13.0 depending on the kind of tissue slice, so that a signal is emitted and the signal from the tissue can be evaluated. It is required that the tissue is not deteriorated too much. The retrieval process is usually performed under a condition of pH 6.0 to 8.0. The retrieval process of a special tissue slice is performed under a condition of pH 3.0, for example.

As for a heater, an autoclave, a microwave heater, a pressure cooker, a water bath, or the like can be used. The retrieval may be performed at any temperature without particular limitation, for example, at room temperature. The temperature may range from 50 to 130° C., and the time may range from 5 to 30 minutes.

Subsequently, the slice after the retrieval process is immersed and washed in PBS in a container. The washing may be performed at any temperature without particular limitation, for example, at room temperature. Each immersion time is preferably 3 minutes or more and 30 minutes or less. The PBS may be replaced with new PBS during the immersion if necessary.

(5.2) Immunostaining Step

In the immunostaining step for staining the objective biological substance, a solution of the immunostaining reagent is put on the slice, and the objective biological substance reacts with the fluorescent nanoparticles including a site which can directly or indirectly bind to the objective biological substance in the solution. The solution of the immunostaining reagent used in the staining step can be prepared in advance before the step.

The conditions for the immunostaining step, i.e. the temperature and time of immersing the tissue sample in the solution of the immunostaining reagent, can be suitably adjusted according to the conventional immunostaining method, so that appropriate signals can be obtained.

The temperature is not particularly limited, and the processing can be performed at room temperature. Preferably, the immersing time is 30 minutes or more and 24 hours or less.

Before performing the above-described processing, it is preferable to add a known blocking reagent such as PBS including BSA and a surfactant such as Tween 20.

(5.3) Post-Processing Step of Sample

After the immunostaining step, the tissue sample is preferably subjected to processes such as fixation and dehydration, permeation, and encapsulation.

The fixation and dehydration process is performed by immersing the tissue sample in a solution for fixation processing (crosslinking reagent such as formalin, paraformaldehyde, glutaraldehyde, acetone, ethanol, and methanol). The permeation process is performed by immersing the tissue sample after the fixation and dehydration process in a solution for permeation (such as xylene). The encapsulation process is performed by immersing the tissue sample after the permeation process in a solution for encapsulation.

The conditions for these processes, i.e. the temperature and time of immersing the tissue sample in the prescribed solution, can be suitably adjusted according to the conventional immunostaining method, so that appropriate signals can be obtained.

(5.4) Staining Step for Morphological Observation

Apart from the immunostaining step, staining for morphological observation is performed for observing morphology of a cell, tissue, and organ in a bright field image.

The staining step for morphological observation can be performed according to a usual method.

For morphological observation of the tissue sample, eosin is generally used for staining cytoplasm, stroma, various fibers, red blood cell, and keratinocyte in red to dark red. Hematoxylin is also generally used for staining a cell nucleus, calcification portion, cartilage, bacteria, and mucus in livid to light blue. (The method to perform these two staining steps simultaneously is known as hematoxylin-eosin staining (HE staining).)

The staining step for morphological observation may be performed after or before the immuno staining step.

[Analysis System]

Analysis system 1 in FIG. 2 is used in the imaging step S2 and analysis step S3.

Analysis system 1 is provided with a microscope 10, an analysis device 20, and a display 30. The microscope 10 is provided with a light source 12 and an imaging camera 14. The microscope 10 is connected to the analysis device 20 to control the microscope 10, and the analysis device 20 is connected with the display 30 to display the microscopic images (see FIGS. 3, 5, and 6), results of processing (see FIGS. 7 to 9), and the like.

[Imaging Step]

(1) Acquisition of Bright Field Image

In the Imaging step S2, the analysis device 20 controls the microscope 10 to acquire an image of the tissue sample A after staining for morphological observation with the imaging camera 14. Subsequently, the analysis device 20 generates a bright field image 100 as in FIG. 3A on the basis of the imaging result by the imaging camera 14.

(2) Acquisition of Fluorescent Image

In the Imaging step S2, apart from the acquisition of the bright field image 100, the analysis device 20 controls the microscope 10 to acquire an immunostaining image with the imaging camera 14. The immunostaining image includes fluorescent bright points and obtained from the same visual field as the bright field image 100. The fluorescent bright points emerge by irradiating the tissue sample after immunostaining with excitation light from the light source 12 to make the fluorescent nanoparticles in the immunostaining reagent emit light. Subsequently, the analysis device 20 generates a fluorescent image 200 as in FIG. 3B on the basis of the imaging result.

Irradiation of excitation light can be performed using a filter for emission light as needed, which selectively transmits the light having prescribed wavelength. In such cases, it is possible to obtain an immunostaining image including only the objective fluorescence by excluding non-objective fluorescence and noises such as excitation light and other light.

[Analysis Step]

In the analysis step S3, the analysis device 20 processes the microscopic images to calculate prescribed statistics and causes the display 30 to display the statistics. The microscopic images are the bright field image 100 and the fluorescent image 200.

Figure 4:
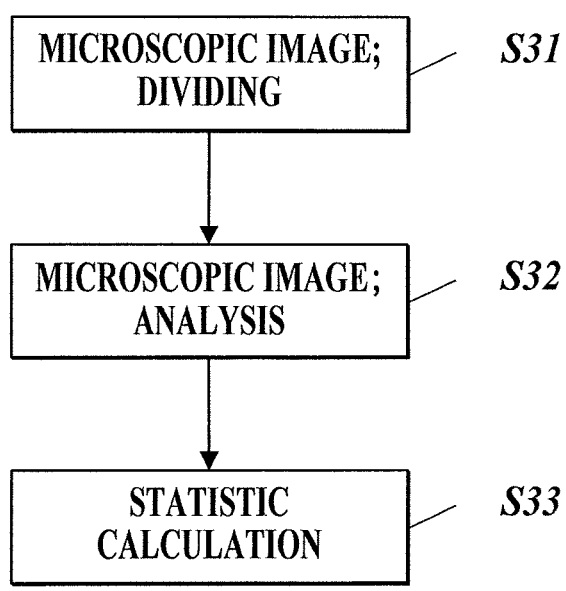
FIG. 4 is a schematic diagram of analysis step.

More specifically, the analysis device 20 mainly performs the following steps as shown in FIG. 4;
(S31) a step of dividing the microscopic images into sections of a prescribed size;
(S32) a step of analyzing staining condition of the microscopic image in each section; and
(S33) a step of calculating a prescribed statistic on the basis of the analysis result.

The analysis device 20 is provided with an operator and a storage. The storage stores an analysis program for the objective biological substance for generating the bright field image 100 and the fluorescent image 200 described above and for performing the processes of steps S31 to S33 in FIG. 4.

The operator reads the analysis program for the objective biological substance, thereby generates the bright field image 100 and the fluorescent image 200 described above, and performs the processes of steps S31 to S33 in FIG. 4.

Figure 5A:
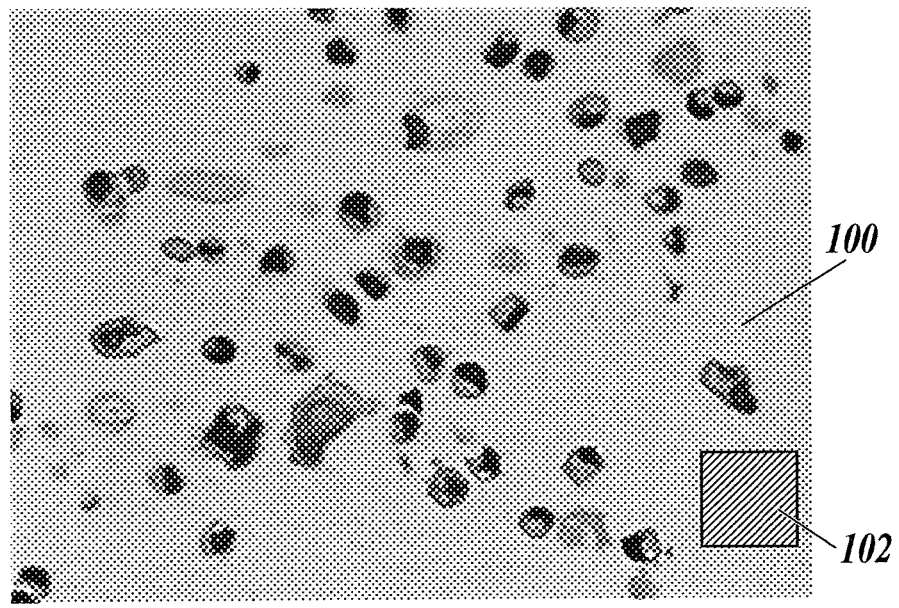
FIG. 5A is a diagram illustrating an exemplary specification in a bright field image.

In the dividing step S31, first of all, as shown in FIG. 5A, a background region 102 is specified in the bright field image 100.

The "background region 102" is a region (reference region) used as a reference in determining an objective section for calculating the number of fluorescent bright points in the analysis step S32 described later. For example, the specified background region includes a region including no cell, a stroma region including no cancer cell, and the like.

Figure 5B:
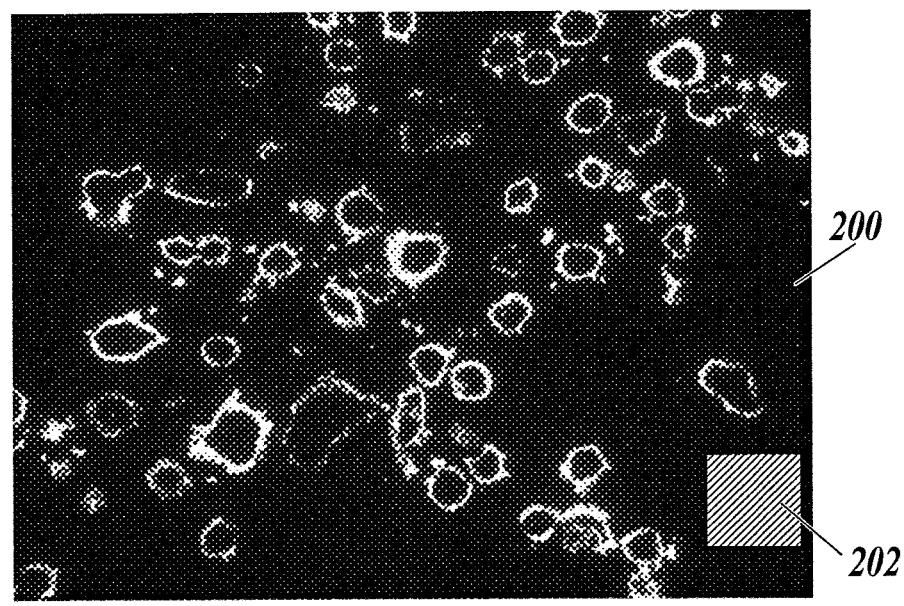
FIG. 5B is a diagram illustrating an exemplary specification a of background region in a fluorescent image.

Subsequently, as shown in FIG. 5B, the background region 202 is specified in the fluorescent image 200. The background region 202 is equivalent to the background region 102 in the bright field image 100. The region without fluorescent bright points in the fluorescent image 200 may be directly specified as the background region 202 without specifying the background region 102 in the bright field image 100.

Figure 6A:
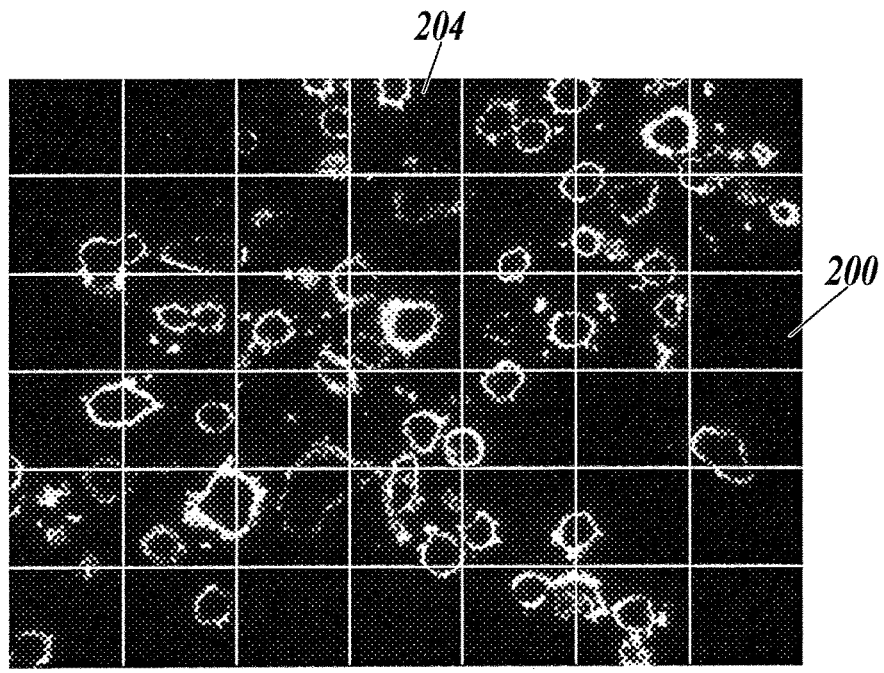
FIG. 6A is a schematic diagram for explanation of analysis step.

Subsequently, as shown in FIG. 6A, a plurality of sections 204 are formed by dividing the fluorescent image 200 into sections having the same size as the background region 202. A plurality of sections may be formed in the fluorescent image 200 in advance and one of the sections may be specified as the background region 202.

In the analysis step S32, the fluorescent image 200 is processed to calculate the number of fluorescent bright points in each of the sections in the fluorescent image 200 which corresponds to the background region 202 and the sections 204.

An example of software used for processing the fluorescent image 200 is "Image J" (open source). Such image processing software allows semiautomatic and rapid calculation of the number of fluorescent bright points having a prescribed luminance value or more.

Figure 6B:
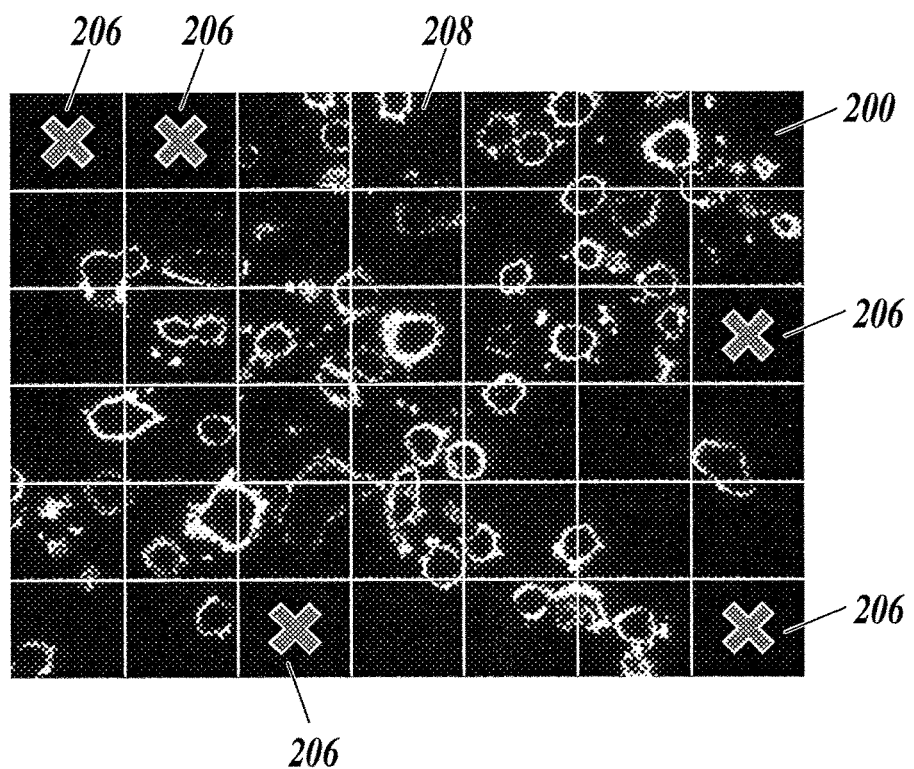
FIG. 6B is a schematic diagram for explanation of analysis step.

Subsequently, it is judged whether or not the number of fluorescent bright points in each of the sections 204 is equal to or more than the number of fluorescent bright points in the background region 202 (reference value in the reference region). As shown in FIG. 6B, a plurality of sections 204 are classified into (i) sections 206 having fluorescent bright points fewer than the background region 202 and (ii) sections 208 having fluorescent bright points equal to or more than the background region 202. The sections 206 are excluded from the analysis target and only the sections 208 are determined as the analysis target. In the classification into the sections 206 and 208, the reference value may be determined by adding a prescribed coefficient to the number of fluorescent bright points in the background region 202.

In the calculation step S33, the average of the numbers of fluorescent bright points in sections 208 is calculated. The average is an example of the statistic. In the example of FIG. 6B, among the sections 204 (42 sections consisting of 6 columns in vertical direction and 7 lines in horizontal direction), five sections 206 are excluded from the analysis target and the remaining 37 sections 208 are determined as the analysis target.

Subsequently, the average of the numbers of fluorescent bright points in sections 208 is plotted in correlation with the quantitative value of protein. As a result, a correlation diagram can be obtained as in FIG. 7.

Figure 7:
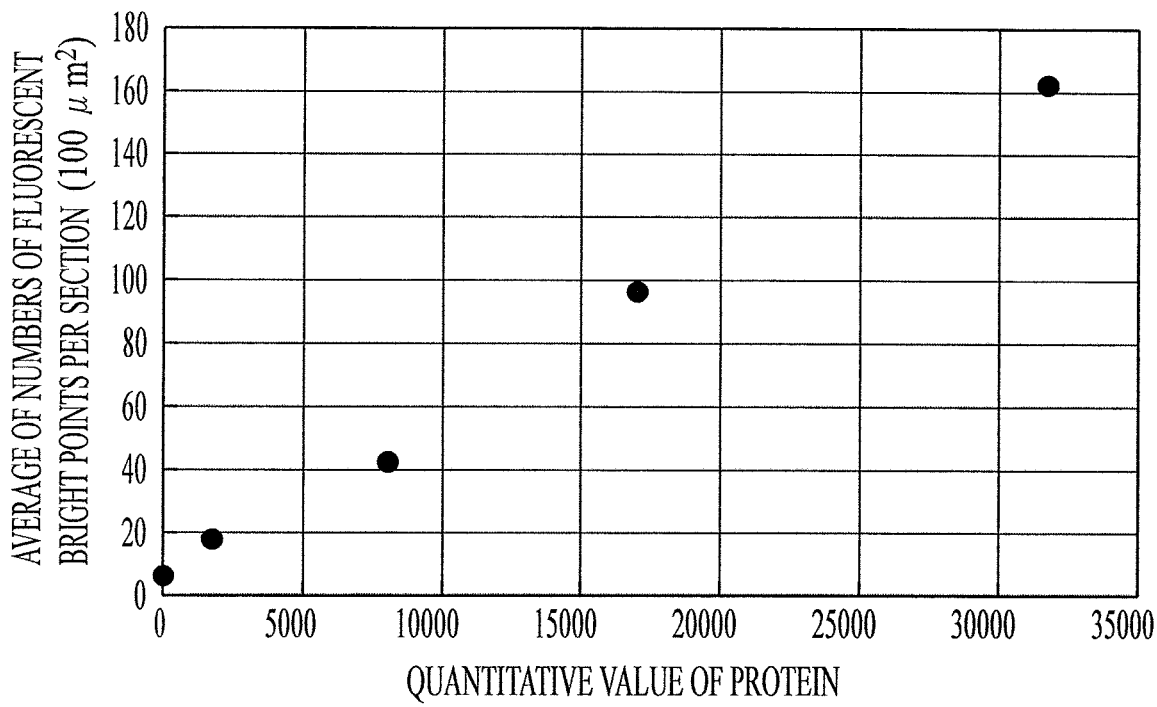
FIG. 7 is a diagram illustrating an exemplary correlation diagram of a statistic (average) and a quantitative value of protein.
Figure 15:
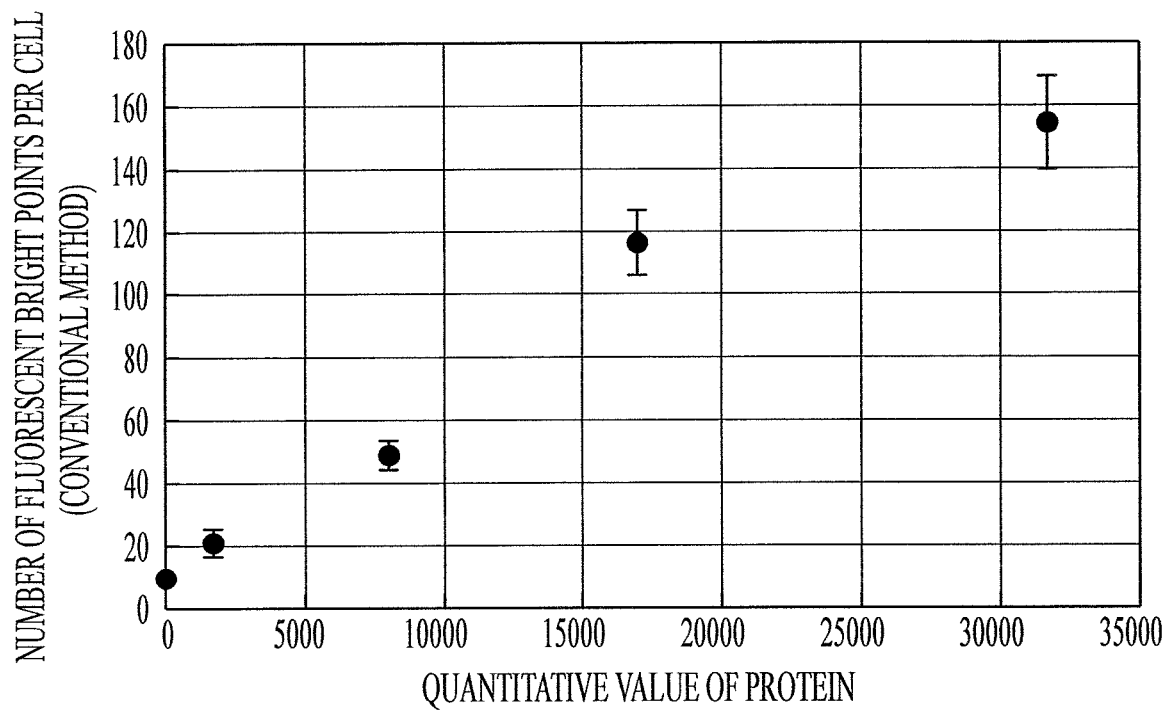
FIG. 15 is a diagram illustrating an exemplary correlation diagram of conventional a statistic (average) and a quantitative value of protein.

The correlation diagram shown in FIG. 7 was obtained from the same sample and under the same condition as in FIG. 15. The correlation coefficient of FIG. 7 was 0.99. The correlation diagram of FIG. 7 was obtained by setting the size (area) of the background regions 102 and 202 and the sections 204 to 100 μm²=10 μm×10 μm.

The size of the background regions 102 and 202 and the sections 204 are preferably set to 100 μm², which is equivalent to the size of one cell.

The size of the background regions 102 and 202 and the sections 204 may be changed. For example, the size may be reduced to 1/10 to 1/2 times of the size of one cell or may be magnified to 2 to 10 times of the size of one cell.

The correlation coefficients are shown in TABLE 1 when the size of the background regions 102 and 202 and the sections 204 are reduced and magnified in obtaining the correlation diagram of FIG. 7. According to the results of TABLE 1, the size of the background regions 102 and 202 and the sections 204 is preferably equivalent to the size of one cell or reduced or magnified to 1/5 to 5 times of the size of one cell.

TABLE 1

| AREA PER SECTION | CORRELATION COEFFICIENT WITH QUANTITATIVE VALUE OF PROTEIN |
|---|---|
| 1/10 TIMES | 0.64 |
| 1/5 TIMES | 0.82 |
| 1/3 TIMES | 0.84 |
| 1/2 TIMES | 0.96 |
| EQUIVALENT TO ONE CELL (100 μm²) | 0.99 |
| 2 TIMES | 0.95 |
| 3 TIMES | 0.88 |

TABLE 1-continued

| AREA PER SECTION | CORRELATION COEFFICIENT WITH QUANTITATIVE VALUE OF PROTEIN |
|---|---|
| 5 TIMES | 0.82 |
| 10 TIMES | 0.68 |

Furthermore, the shape of the background regions 102 and 202 and the sections 204 is not limited to be in a square shape but may be in a polygonal shape, circular shape, or honeycomb shape.

According to the embodiment of the present invention, on the basis of the number of the fluorescent bright points in the background region 202, a plurality of sections 204 are classified into the sections 206 which are not analysis targets and the sections 208 which are analysis targets. Because only the sections 208 are the analysis target for calculating the average of the number of fluorescent bright points, the statistic can be uniquely and rapidly calculated. Accordingly, the analysis time can be shortened while suppressing variations in statistic depending on the kind of tissue slice and the diagnostician.

Modified Example 1

In the calculation step S33, the statistic may be the median of the numbers of fluorescent bright points.

That is, in the analysis step 32, all the sections 204 are determined as the analysis target. In the calculation step 33, the numbers of the fluorescent bright points in the sections 204 are added and the median of the total number is determined as the statistic. For example, when the total number of the fluorescent bright points in all the sections 204 is 160, the median is 80.

Subsequently, the median of the numbers of fluorescent bright points in sections 204 is plotted in correlation with the quantitative value of protein. As a result, a correlation diagram can be obtained as in FIG. 8.

Figure 8:
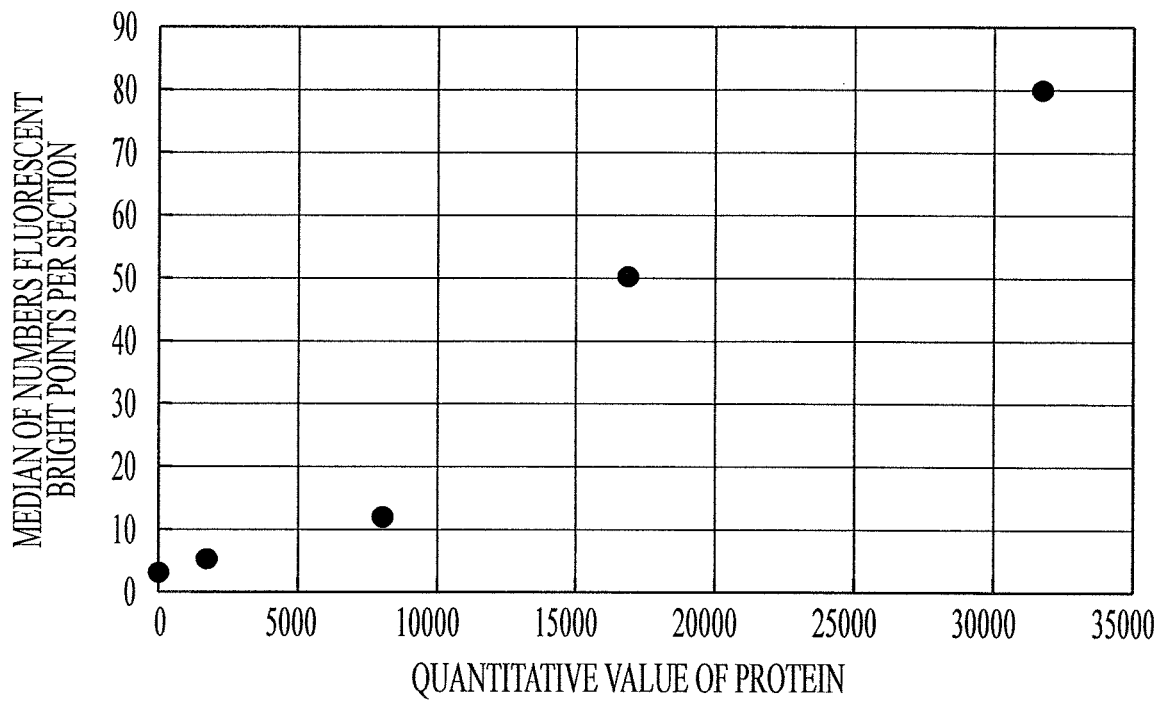
FIG. 8 is a diagram illustrating an exemplary correlation diagram of a statistic (median) and a quantitative value of protein.

The correlation diagram shown in FIG. 8 was also obtained from the same sample and under the same condition as in FIG. 15. The correlation coefficient of FIG. 8 was 0.98.

According to the modified example 1, the classification into the sections 206 and 208 or the specification of background regions 102 and 202 in the dividing step S31 are not necessary.

Modified Example 2

In the calculation step S33, the statistic may be a peak value of a histogram of the fluorescent bright points.

That is, in the analysis step 32, all the sections 204 are determined as the analysis target. In the calculation step, a histogram is generated by calculating the number of the fluorescent bright points per one section 204 and the ratio of the sections 204 including a certain number of fluorescent bright points to all the sections 204. The class value corresponding to the peak of the histogram of each cell line is determined as the statistic.

A diagram in FIG. 9 is an exemplary histogram obtained from the same sample and under the same condition as in FIG. 15.

In FIG. 9, the horizontal axis shows the number of the fluorescent bright points and the vertical axis shows the ratio of the sections 204 including a certain number of fluorescent bright points to all the sections 204.

Regarding SKOV-3 in FIG. 9, for example, the sections including ten fluorescent bright points make up the largest ratio (20%) and the class value (class 10) corresponding to the peak value (20%) is determined as the statistic. Similarly, the class value regarding A549 is 13, the class value regarding Calu3 is 15, the class value regarding T47D is 19, and the class value regarding MCF7 is 21. These class values are determined as the statistics.

Subsequently, the class value corresponding to the peak of the histogram of the fluorescent bright points is plotted in correlation with the quantitative value of protein. As a result, a correlation diagram can be obtained. The correlation coefficient of FIG. 7 was 0.98.

According to the modified example 2, the classification into the sections 206 and 208 or the specification of background regions 102 and 202 in the dividing step S31 are not necessary.

Second Embodiment

The second embodiment is the same as the first embodiment except for the following points.

[Staining Step]

In the staining step S1, in addition to the tissue sample A including an objective biological substance, a tissue sample B including no objective biological substance is also prepared. Immunostaining and morphological observation staining of the tissue samples A and B are performed using a staining reagent for immunostaining and a staining reagent for morphological observation.

The "tissue sample B including no objective biological substance" is a tissue sample of a cultured cell and the like and does not express the objective protein to be detected or quantitated.

The second embodiment is described in the case when a tissue sample of a mouse osteosarcoma cell line LM8 (cultured cell) is used as the tissue sample B including no objective biological substance.

[Imaging Step]

Figure 3B:
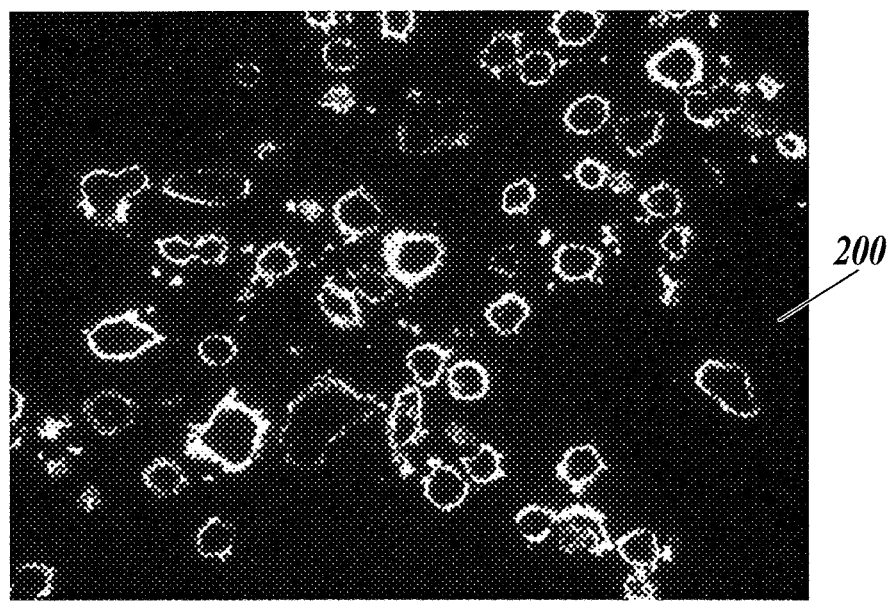
FIG. 3B is a diagram illustrating an exemplary fluorescent image.
Figure 10A:
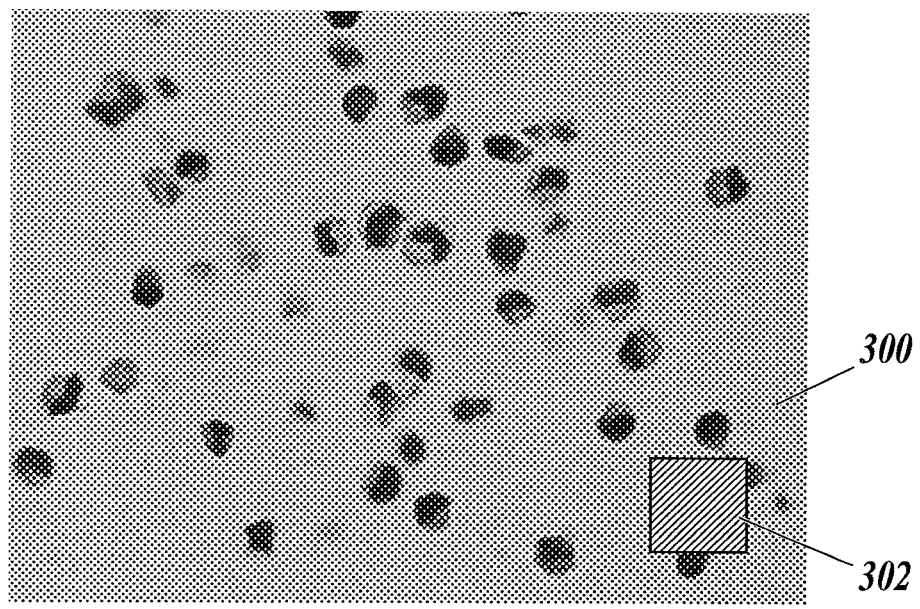
FIG. 10A is a diagram illustrating an exemplary bright field image of tissue sample without objective biological substance, according to the second embodiment.

In the Imaging step S2, just as the bright field image 100 and the fluorescent image 200 in FIG. 3A are generated from the tissue sample A after morphological observation, a bright field image 300 and a fluorescent image 400 in FIG. 10A are generated from the tissue sample B after morphological observation.

Figure 10B:
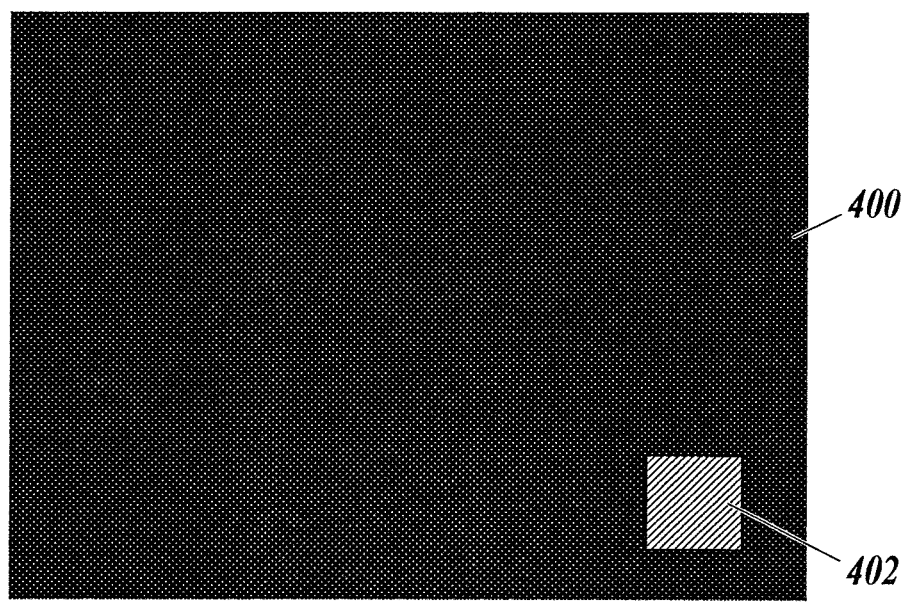
FIG. 10B is a diagram illustrating an exemplary fluorescent image of tissue sample without objective biological substance, according to the second embodiment.

Because the tissue sample B does not include the objective biological substance, fluorescent bright points are not basically observed as in FIG. 10B.

[Analysis Step]

In the dividing step S31, first of all, as shown in FIG. 10A, a background region 302 is specified in the bright field image 300.

The "background region 302" is a region used as a reference in determining an objective section for calculating the number of fluorescent bright points in the analysis step S32 described later, in place of the background region 102.

Subsequently, as shown in FIG. 10B, the region in the fluorescent image 400 equivalent to the background region 302 in the bright field image 300 is specified as the background region 402. The region without fluorescent bright points in the fluorescent image 400 may be directly specified as the background region 402 without specifying the background region 302 in the bright field image 300.

As described above, because the tissue sample B does not include the objective biological substance and fluorescent bright points are not basically observed, the background regions 302 and 402 can be specified as any region in the bright field image 300 and the fluorescent image 400.

Subsequently, as shown in FIG. 6A, a plurality of sections 204 is formed by dividing the fluorescent image 200 into sections having the same size as the background region 402.

In the analysis step S32, the background region 402 in FIG. 10B is substituted for the background region 202 in FIG. 5B and the same processes are performed as the first embodiment.

As a result, in the calculation step S33, a correlation diagram as in FIG. 11 can be obtained corresponding to FIG. 7.

A correlation diagram in FIG. 11 was obtained from the same sample and under the same condition as in FIG. 15. The correlation coefficient of FIG. 11 was 0.99. The correlation diagram of FIG. 11 has an accuracy equivalent to that of FIG. 7. The correlation diagram of FIG. 11 was also obtained by setting the size (area) of the background regions 302 and 402 and the sections 204 to 100 $\mu m^2$ (10 $\mu m$ by 10 $\mu m$).

The size of the background regions 302 and 402 and the sections 204 are preferably set to 100 $\mu m^2$, which is equivalent to the size of one cell.

The size of the background regions 302 and 402 and the sections 204 may be changed. For example, the size may be reduced to $1/10$ to $1/2$ times of the size of one cell or may be magnified to 2 to 10 times of the size of one cell.

Furthermore, the shape of the background regions 302 and 402 and the sections 204 is not limited to be in a square shape but may be in a polygonal shape, circular shape, or honeycomb shape.

According to the second embodiment described above, the tissue sample B including no objective biological substance is prepared, the bright field image 300 and the fluorescent image 400 are generated to specify the background regions 302 and 402, and the statistics are calculated on the basis of the background region 402.

The experiment for obtaining the correlation diagram as in FIG. 7 according to the first embodiment and the experiment for obtaining the correlation diagram as in FIG. 11 according to the second embodiment are respectively repeated eight times to examine the duplicability for the five cell lines (SKOV-3, A549, Calu3, T47D, and MCF7). While the CV value ((coefficient of variation)=(standard deviation)/(average value)) was about 8% according to the experiment for obtaining the correlation diagram as in FIG. 7, the CV value was improved to 6.2% according to the experiment for obtaining the correlation diagram as in FIG. 11. Accordingly, the variations in statistics can be effectively suppressed in particular, by specifying the background region 402 from the tissue sample B including no objective biological substance.

Third Embodiment

The third embodiment is the same as the first embodiment except for the following points.
[Staining Step]

In the staining step S1, a tissue sample C of a tissue itself including an objective biological substance is prepared. Immunostaning and morphological observation staining of the tissue sample C are performed using a staining reagent for immunostaining and a staining reagent for morphological observation.

The "tissue (itself)" is a biological structure larger than a cell, such as a blood vessel, a lymphatic vessel, a glomerulus, a duct, a breast duct, and a follicle.

The third embodiment is described in the case when a tissue sample of a senile plaque (a tissue of a brain with Alzheimer's disease) was used as the tissue sample C and stained using an anti-amyloid $\beta$ antibody.
[Imaging Step]

Figure 12A:
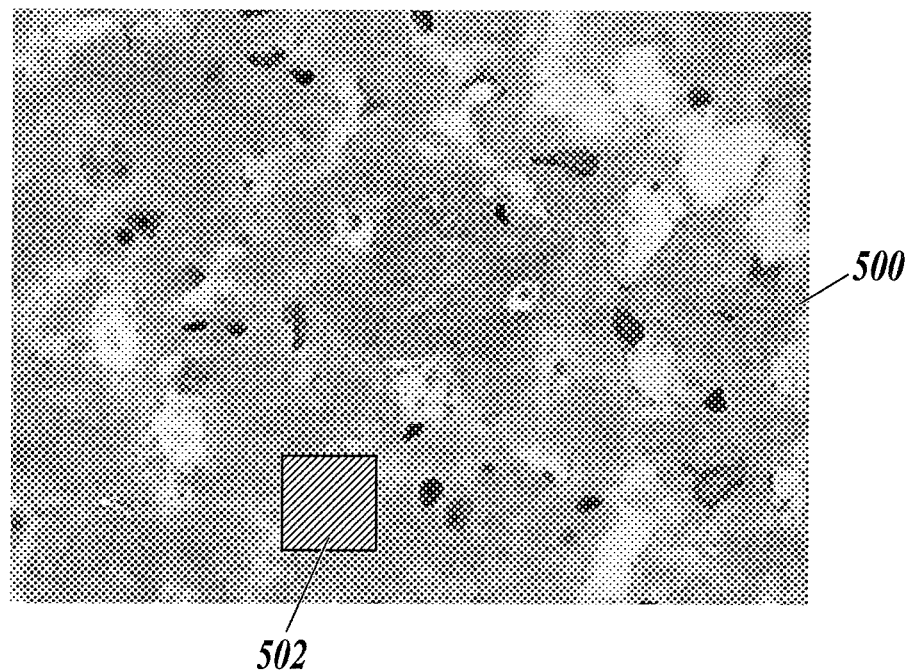
FIG. 12A is a diagram illustrating an exemplary specification a of background region in a bright field image according to the third embodiment.

In the Imaging step S2, just as the bright field image 100 and the fluorescent image 200 in FIG. 3A are generated from the tissue sample A after morphological observation, a bright field image 500 and a fluorescent image 600 in FIG. 12A are generated from the tissue sample C after morphological observation.
[Analysis Step]

In the analysis step S3, the bright field image 500 and the fluorescent image 600 are substituted for the bright field image 100 and the fluorescent image 200 and the same processes are performed as the first embodiment.

That is, in the analysis step S3, the analysis device 20 processes the microscopic images to calculate prescribed statistics and causes the display 30 to display the statistics. The microscopic images are the bright field image 500 and the fluorescent image 600.

In the dividing step S31, first of all, as shown in FIG. 12A, a background region 502 is specified in the bright field image 500.

The "background region 502" is a region used as a reference in determining an objective section for calculating the number of fluorescent bright points in the analysis step S32 described later. The background region 502 is specified in the region without senile plaque.

Figure 12B:
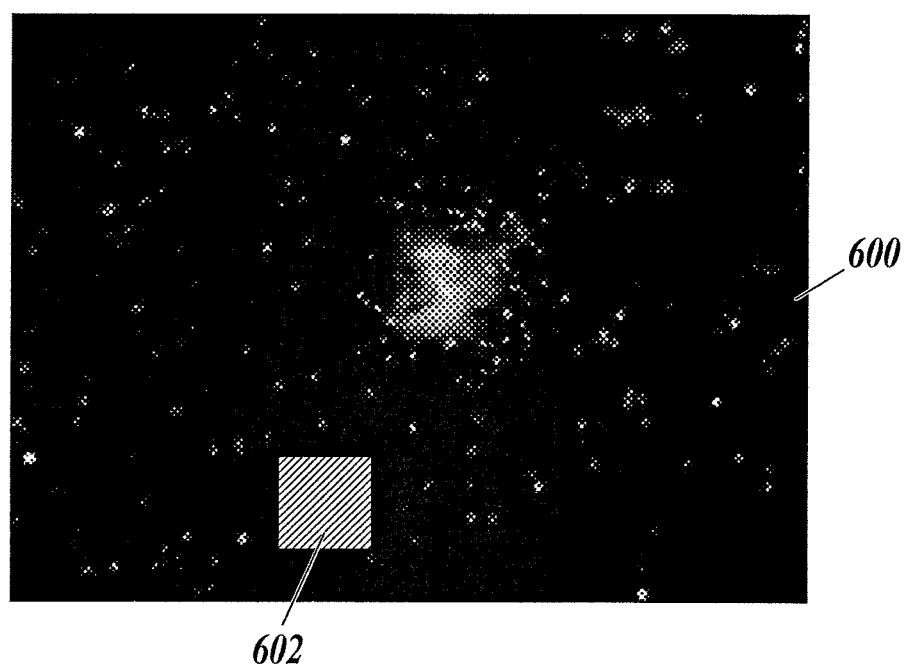
FIG. 12B is a diagram illustrating an exemplary specification a of background region in a fluorescent image according to the third embodiment.

Subsequently, as shown in FIG. 12B, the region in the fluorescent image 600 equivalent to the background region 502 in the bright field image 500 is specified as the background region 602. The region without fluorescent bright points in the fluorescent image 600 may be directly specified as the background region 602 without specifying the background region 502 in the bright field image 500.

Figure 13A:
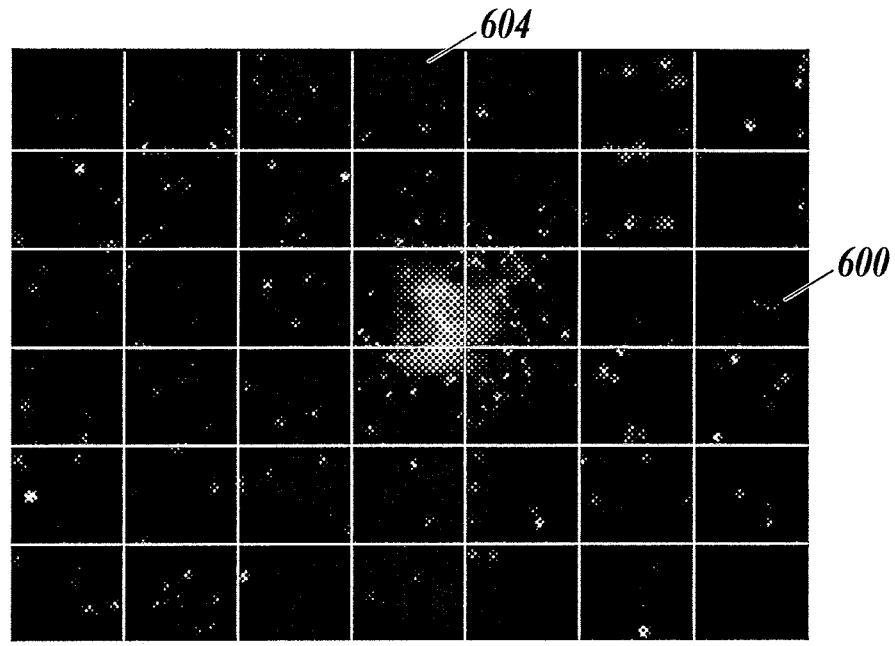
FIG. 13A is a schematic diagram for explanation of analysis step according to the third embodiment.

Subsequently, as shown in FIG. 13A, a plurality of sections 604 are formed by dividing the fluorescent image 600 into sections having the same size as the background region 602. A plurality of sections may be formed in the fluorescent image 600 in advance and one of the sections may be specified as the background region 602.

In the analysis step S32, the fluorescent image 600 is processed to calculate the number of fluorescent bright points in each of the sections in the fluorescent image 600 which corresponds to the background region 602 and the sections 604.

Figure 13B:
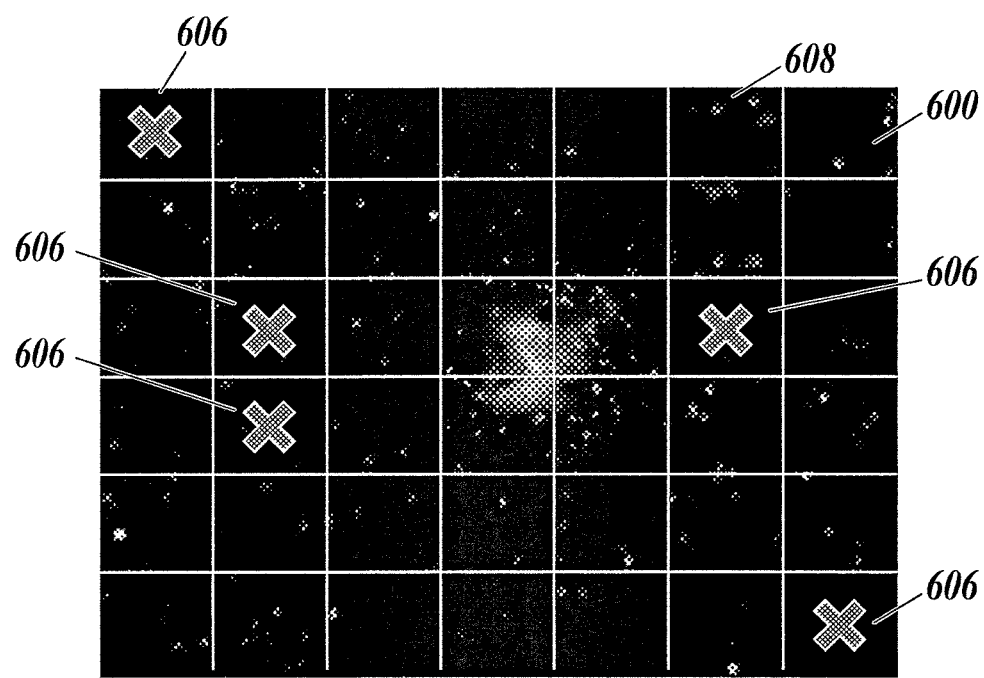
FIG. 13B is a schematic diagram for explanation of analysis step according to the third embodiment.

Subsequently, it is judged whether or not the number of fluorescent bright points in the sections 604 is equal to or more than the number of fluorescent bright points in the background region 602. As shown in FIG. 13B, a plurality of sections 604 are classified into (i) sections 606 having fluorescent bright points fewer than the background region 602 and (ii) sections 608 having fluorescent bright points equal to or more than the background region 602. The sections 606 are excluded from the analysis target and only the sections 208 are determined as the analysis target. In the classification into the sections 606 and 608, the reference value may be determined by adding a prescribed coefficient to the number of fluorescent bright points in the background region 602.

In the calculation step S33, the average of the numbers of fluorescent bright points in sections 608 is calculated. The average is an example of the statistics. In the example of FIG. 13B, among the sections 604 (42 sections consisting of 6 columns in vertical direction and 7 lines in horizontal direction), five sections 606 are excluded from the analysis target and remaining 37 sections 608 are determined as the analysis target.

Subsequently, the average of the numbers of fluorescent bright points in sections 608 is plotted in correlation with the number of the fluorescent bright points measured visually per unit area (400 µm$^2$) from a region (20 µm×20 µm=400 µm$^2$) of a senile plaque visually identified in the fluorescent image 600. As a result, a correlation diagram can be obtained as in FIG. 14.

Figure 14:
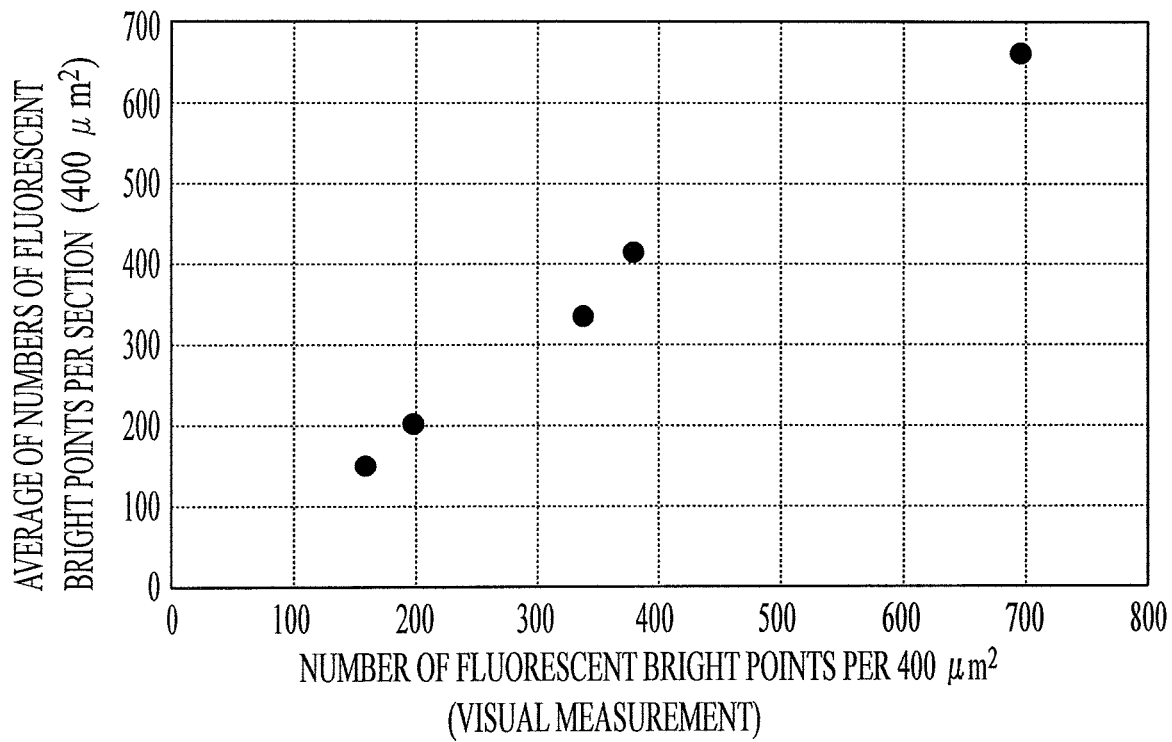
FIG. 14 is a diagram illustrating an exemplary correlation diagram of a statistic (average) according to the third embodiment and a number of visually-measured fluorescent bright points per unit area.

FIG. 14 shows a correlation diagram of five samples of Alzheimer's disease. The correlation coefficient of FIG. 14 was 0.99. The correlation diagram of FIG. 14 was obtained by setting the size (area) of the background regions 502 and 602 and the sections 604 to 20 µm×20 µm=400 µm$^2$.

The size of the background regions 502 and 602 and the sections 604 are preferably set to the size equivalent to that of one tissue.

Here, the size of the background regions 502 and 602 and the sections 604 are preferably set to the size equivalent to that of a senile plaque.

The size of the background regions 502 and 602 and the sections 604 may be changed. For example, the size may be reduced to 1/10 to 1/2 times of the size of one tissue or may be magnified to 2 to 10 times of the size of one tissue.

The correlation coefficients are shown in TABLE 2 when the size of the background regions 502 and 602 and the sections 604 are reduced and magnified in obtaining the correlation diagram of FIG. 14. According to the results of TABLE 2, the size of the background regions 502 and 602 and the sections 604 is preferably equivalent to the size of one senile plaque, or reduced or magnified to 1/5 to 5 times of one senile plaque.

TABLE 2

| AREA PER SECTION | CORRELATION COEFFICIENT WITH VISUALLY-MEASURED VALUE |
| --- | --- |
| 1/10 TIMES | 0.44 |
| 1/5 TIMES | 0.80 |
| 1/3 TIMES | 0.82 |
| 1/2 TIMES | 0.94 |
| EQUIVALENT TO SENILE PLAQUE (400 µm$^2$) | 0.99 |
| 2 TIMES | 0.92 |
| 3 TIMES | 0.81 |
| 5 TIMES | 0.80 |
| 10 TIMES | 0.48 |

Furthermore, the shape of the background regions 502 and 502 and the sections 604 is not limited to be in a square shape but may be in a polygonal shape, circular shape, or honeycomb shape.

According to the third embodiment described above, the tissue sample C of a tissue itself including an objective biological substance is prepared and used to calculate the statistics. Similar effects as the first embodiment can be achieved even by changing the tissue sample from cell level to tissue level.

As in the modified examples 1 and 2 of the first embodiment, the statistic according to the third embodiment may be the median of the numbers of fluorescent bright points or the peak value of the histogram of the fluorescent bright points.

The third embodiment may be performed as follows; the tissue sample of a tissue itself including no objective biological substance is prepared as in the second embodiment; the bright field image and the fluorescent image are generated from the tissue sample to specify a background region; and the statistics are calculated on the basis of the background region. Examples of the "tissue sample of a tissue itself including no objective biological substance" regarding a senile plaque includes, in the case of experiments on animals such as mouse, tissue samples of a brain of juvenile animals, stroma, a skeletal muscle, and the like.

Fourth Embodiment

The fourth embodiment is the same as the first embodiment except that the following "[STAINING STEP USING FLUORESCENT NANOPARTICLE BONDED TO A BIOLOGICAL SUBSTANCE RECOGNITION SITE]" is substituted for the "(5.2) Immunostaining step" described in the first embodiment.

[Staining Step Using Fluorescent Nanoparticle Bonded to a Biological Substance Recognition Site]

A PBS dispersion of fluorescent nanoparticles bonded to a biological substance recognition site is put on the tissue slice so as to be reacted with the objective biological substance. By changing the biological substance recognition site, to which is the fluorescent nanoparticles are bonded, a variety of biological substances can be stained. When fluorescent nanoparticles bonded to multiple kinds of the biological substance recognition site are used, PBS dispersions of the respective fluorescent nanoparticles may be mixed in advance, or may be put on the tissue slice individually and successively.

The temperature is not particularly limited, and the processing can be performed at room temperature. Preferably, the reacting time is 30 minutes or more and 24 hours or less.

Preferably, a well-known blocking agent such as BSA-containing PBS is dripped before staining with the fluorescent nanoparticles.

Next, the stained tissue slice is immersed in a container containing PBS so that the unreacted fluorescent nanoparticles are removed. The temperature is not particularly limited, and the processing can be performed at room temperature. Preferably, the immersing time is 3 minutes or more and 30 minutes or less. The PBS may be changed during the immersion as needed. A cover glass is placed on the tissue slice to seal. A commercially available sealing agent may be used as needed.

When staining with an HE staining reagent is performed, the HE staining is performed before sealing with the cover glass is performed. As a result, the measurement data of bright points could be obtained, which us equivalent to the results according to the first embodiment.

The above-described first to fourth embodiments are not limited to the above-described examples but can be appropriately improved.

For example, in the first to fourth embodiments (including modified examples 1 and 2), the number of fluorescent bright points of the fluorescent images 200 and 600 are calculated in the step of analyzing staining conditions of the microscopic image.

Otherwise, statistic may be calculated on the basis of the calculation results of chromaticity, intensity of each color, and area of each color, and the like.

Furthermore, the background region, the region including no cell, and the stroma region including no cancer cell may be automatically specified by the analysis device of the objective biological substance according to the present invention from the bright field image, the fluorescent image, or the fluorescent image without operation via an operation portion by an operator etc.

INDUSTRIAL APPLICABILITY

As described above, the present invention is suitable for providing an analysis device, an analysis system, an analysis method, and an analysis program for an objective biological substance which can shorten the analysis time while suppressing variations in statistics depending on the kind of tissue slice and the diagnostician.

DESCRIPTION OF REFERENCE NUMERALS

1 Analysis system
10 Microscope
12 Light source
14 Imaging camera
20 Analysis device
30 Display Although embodiments of the present invention have been described and illustrated in detail, it is clearly understood that the same is by way of illustration and example only and not limitation, and the scope of the present invention should be interpreted by terms of the appended claims.

The invention claimed is:

1. An analysis device for an objective biological substance, comprising
a generator that generates a fluorescent image as a microscopic image of a tissue sample after staining;
a divider that divides the microscopic image into at least one section having a prescribed size;
an analyzer that analyzes the fluorescence of the microscopic image for each section; and
a calculator that calculates a prescribed statistic based on an analysis result by the analyzer;
wherein the divider specifies a reference region containing no cells to determine at least one analysis target section;
wherein the analyzer determines the analysis target section satisfying a reference for the reference region from the section divided by the divider and calculates a number of fluorescent bright points in the fluorescent image for each analysis target section;
wherein the analysis target section is determined to be a section which contains fluorescent bright points greater than or equal to the reference region;
wherein the calculator calculates the statistic based on the number of fluorescent bright points in the analysis target section.

2. The analysis device for an objective biological substance according to claim 1, wherein
the divider divides the microscopic image into at least one section having a size equivalent to a size of one cell or one tissue or having a size reduced or magnified to 1/5 to 5 times of the size of one cell or one tissue.

3. The analysis device for an objective biological substance according to claim 1, wherein
the generator generates a second microscopic image of a tissue sample including no objective biological substance after staining, and
the divider specifies a reference region to determine the analysis target section to be analyzed by the analyzer in the second microscopic image.

4. The analysis device for an objective biological substance according to claim 1, wherein the generator generates a fluorescent image as the microscopic image,
the analyzer calculates a number of fluorescent bright point in the fluorescent image for each analysis target section, and
the calculator calculates an average of the number of fluorescent bright point in the analysis target section as the statistic.

5. The analysis device for an objective biological substance according to claim 1, wherein
the generator generates a fluorescent image as the microscopic image,
the analyzer determines all of the section divided by the divider as an analysis target section, and
the calculator calculates a median of number of fluorescent bright point in the analysis target section as the statistic.

6. The analysis device for an objective biological substance according to claim 1, wherein
the generator generates a fluorescent image as the microscopic image,
the analyzer determines all of the section divided by the divider as an analysis target section, and
the calculator calculates a class value corresponding to a peak of a histogram of number of fluorescent bright point in the analysis target section as the statistic.

7. The analysis device for an objective biological substance according to claim 1, wherein
the generator generates a fluorescent image as the microscopic image, and
the calculator calculates a median of number of fluorescent bright point in the analysis target section as the statistic.

8. The analysis device for an objective biological substance according to claim 1, wherein
the generator generates a fluorescent image as the microscopic image, and
the calculator calculates a class value corresponding to a peak of a histogram of number of fluorescent bright point in the analysis target section as the statistic.

9. The analysis device for an objective biological substance according to claim 1, wherein the reference region is specified automatically.

10. The analysis device for an objective biological substance according to claim 1, wherein the section is in a square shape, a polygonal shape, a circular shape, or a honeycomb shape.

11. The analysis system for an objective biological substance, comprising:
a microscope that images a tissue sample after staining; and
the analysis device for the objective biological substance according to claim 1 that receives an imaging result by the microscope.

12. An analysis method for an objective biological substance, comprising:
generating a microscopic image of a tissue sample after staining;
dividing the microscopic image into at least one section having a prescribed size;
analyzing the staining condition of the microscopic image for each section; and
calculating a prescribed statistic based on an analysis result in the analyzing;
wherein the dividing specifies a reference region to determine at least one analysis target section to be analyzed by the analyzer, wherein the analyzer determines the analysis target section satisfying a reference for the reference region from the section divided by the dividing, wherein the analysis target section is determined to be a section which contains fluorescent bright points greater than or equal to the reference region, and wherein the calculator calculates the statistic based on the number of fluorescent bright points in the analysis target section.

13. A non-transitory recording medium storing a computer readable analysis program for an objective biological substance causing a computer to function as:

a generator that generates a microscopic image of a tissue sample after staining;

a divider that divides the microscopic image into at least one section having a prescribed size;

an analyzer that analyzes a staining condition of the microscopic image for each section; and a calculator that calculates a prescribed statistic based on an analysis result by the analyzer;

wherein the divider specifies a reference region to determine at least one analysis target section to be analyzed by the analyzer, wherein the analyzer determines the analysis target section satisfying a reference for the reference region from the section divided by the divider, wherein the analysis target section is determined to be a section which contains fluorescent bright points greater than or equal to the reference region, and wherein the calculator calculates the statistic based on the number of fluorescent bright points in the analysis target section.

\* \* \* \* \*